(12) United States Patent
Spencer et al.

(10) Patent No.: US 8,215,173 B2
(45) Date of Patent: Jul. 10, 2012

(54) UT METHOD OF IDENTIFYING A STUCK JOINT

(76) Inventors: Roger Spencer, Ashville, OH (US); Margarit Lozev, Lewis Center, OH (US); Ta-Chieh Huang, Dublin, OH (US)

( * ) Notice: Subject to any disclaimer, the term of this patent is extended or adjusted under 35 U.S.C. 154(b) by 920 days.

(21) Appl. No.: 12/186,047

(22) Filed: Aug. 5, 2008

(65) Prior Publication Data

US 2010/0031750 A1   Feb. 11, 2010

(51) Int. Cl.
*G01N 24/00* (2006.01)
(52) U.S. Cl. ......................................................... 73/620
(58) Field of Classification Search ................ 73/570, 73/584, 587, 620, 627
See application file for complete search history.

(56) References Cited

U.S. PATENT DOCUMENTS

| | | | |
|---|---|---|---|
| 3,895,685 A * | 7/1975 | Gillette et al. | 181/0.5 |
| 3,978,714 A * | 9/1976 | Shraiber et al. | 73/625 |
| 4,274,289 A * | 6/1981 | Weiss et al. | 73/618 |
| 4,327,738 A | 5/1982 | Green et al. | |
| 4,344,159 A | 8/1982 | Ballinger | |
| 4,442,715 A | 4/1984 | Brisken et al. | |
| 4,534,221 A | 8/1985 | Fife et al. | |
| 4,631,710 A | 12/1986 | Yamaguchi et al. | |
| 4,642,215 A * | 2/1987 | Klinvex et al. | 376/249 |
| 4,744,250 A | 5/1988 | Ganglbauer et al. | |
| 4,770,699 A | 9/1988 | Mountford | |
| 4,836,026 A | 6/1989 | P'An et al. | |
| 4,865,040 A | 9/1989 | Ogasawara | |
| 4,886,069 A | 12/1989 | O'Donnell | |
| 5,030,911 A | 7/1991 | Lam | |
| 5,063,780 A | 11/1991 | Landry et al. | |
| 5,121,364 A | 6/1992 | O'Donnell | |
| 5,142,649 A | 8/1992 | O'Donnell | |
| 5,278,757 A | 1/1994 | Hoctor et al. | |
| 5,282,471 A | 2/1994 | Sato | |
| 5,299,577 A | 4/1994 | Brown et al. | |
| 5,331,964 A | 7/1994 | Trahey et al. | |
| 5,487,306 A | 1/1996 | Fortes | |
| 5,513,532 A * | 5/1996 | Beffy et al. | 73/628 |
| 5,531,117 A | 7/1996 | Fortes | |
| 5,549,111 A | 8/1996 | Wright et al. | |

(Continued)

OTHER PUBLICATIONS

Moles et al., "Pipeline Girth Weld Inspections using Ultrasonic Phased Arrays," Pan-American Conference for Nondestructive Testing, Rio De Janeiro, Brazil, Jun. 6, 2003, entire document.

(Continued)

*Primary Examiner* — Max Noori
(74) *Attorney, Agent, or Firm* — McNees Wallace & Nurick, LLC (57) ABSTRACT

An ultrasonic testing method to identify a stuck joint between two workpieces utilizing an ultrasonic probe to transmit ultrasonic (US) beams into the joint area and capture the associated US reflections. The method transmits two separate US beams fired in very close proximity to one another. The probe then captures a plurality of US reflections. The method looks for subtle variations in a high gain A-scan presentation of a high gain reflected beam, while using a low gain US beam to identify the particular region on the high gain A-scan presentation in which to look for signs of a stuck joint. Subtle variations within a particular region of the high gain A-scan presentation identify stuck joints. The method is applicable to metals and nonmetals and is not limited to fusion welding, but may also be used with solid state welds, brazed and soldered joints, and adhesively joined workpieces.

20 Claims, 8 Drawing Sheets

U.S. PATENT DOCUMENTS

| | | | |
|---|---|---|---|
| 5,677,490 | A | 10/1997 | Gunther et al. |
| 5,777,891 | A | 7/1998 | Pagano et al. |
| 5,797,844 | A | 8/1998 | Yoshioka et al. |
| 5,797,847 | A | 8/1998 | Miller et al. |
| 6,055,862 | A * | 5/2000 | Martens .................. 73/632 |
| 6,254,542 | B1 | 7/2001 | Hamilton et al. |
| 6,279,397 | B1 | 8/2001 | Dwyer |
| 6,332,011 | B1 | 12/2001 | Johnson |
| 6,344,739 | B1 | 2/2002 | Hardy et al. |
| 6,484,584 | B2 | 11/2002 | Johnson et al. |
| 6,532,820 | B1 | 3/2003 | Fleming et al. |
| 6,640,632 | B1 | 11/2003 | Hatanaka et al. |
| 6,676,603 | B2 | 1/2004 | Aichhorn et al. |
| 6,732,587 | B2 | 5/2004 | Lorraine et al. |
| 6,813,950 | B2 | 11/2004 | Glascock et al. |
| 6,865,243 | B2 | 3/2005 | Paillaman et al. |
| 6,911,008 | B2 | 6/2005 | Pelissier |
| 6,920,791 | B2 | 7/2005 | Wagner et al. |
| 6,925,882 | B1 | 8/2005 | Fleming et al. |
| 6,931,931 | B2 | 8/2005 | Graff et al. |
| 6,945,937 | B2 | 9/2005 | Culp et al. |
| 6,948,369 | B2 | 9/2005 | Fleming et al. |
| 6,957,583 | B2 | 10/2005 | Tooma et al. |

OTHER PUBLICATIONS

International Searching Authority (USPTO), International Search Report and Written Opinion for International Application No. PCT/US2009/049428, mailed Aug. 31, 2009, 8 pages.

Dr. Michael D. C. Moles et al., Introduction to Phased Array Ultrasonic Technology Applications, 2004, pp. 6-18, R/D Tech, Inc., Canada.

* cited by examiner

UT METHOD OF IDENTIFYING A STUCK JOINT

STATEMENT REGARDING FEDERALLY SPONSORED RESEARCH OR DEVELOPMENT

This invention was not made as part of a federally sponsored research or development project.

TECHNICAL FIELD

The present invention relates to the field of nondestructive evaluation, namely ultrasonic evaluation of joints to determine if a stuck, or cold, weld or bond is present.

BACKGROUND OF THE INVENTION

Sheet metal joining processes are widely used in many industries, such as the aerospace and automotive industries. Among these processes, resistance spot welding is the most common procedure used to join metal sheets because it has high process speed and is easily adopted in mass production lines; however, seam welding, weld bonding, adhesive joining, soldering, and brazing are gaining more widespread acceptance. The quality control of such joining processes is an important issue to manufacturers.

The quality of such joints is affected by the joining process itself and the design of the joint. Many factors have to be taken into account, such as metallurgic reactions, thermal behaviors, chemical composition, condition of the base metal, welding and bonding conditions, and the welding and bonding equipment. Furthermore, the intricate relationship between these factors makes it more difficult to control the quality of the joint, and difficult to inspect the joint in a nondestructive manner.

Acoustic methods are commonly used nondestructive testing methods that have been used for various inspection applications. Unlike other nondestructive testing methods, the acoustic method provides both surface and internal information. Moreover, the acoustic method allows deeper penetration into specimens and higher sensitivity to small discontinuities. Acoustic methods, however, are not flawless. The most significant limitations include the requirement of skillful operators for operating the device and analyzing the acoustic information, as well as the very subjective nature of identifying a stuck, or cold, weld or inadequate bond, such as a kissing bond.

The field of ultrasonic nondestructive evaluation (NDE) inspection techniques has needed a reliable way of identifying poor quality joints in a manner that eliminates the need for a skilled operator while still providing improved reliability by eliminating the subjective nature of prior techniques. While some of the prior art devices have attempted to improve the state of the art, none has achieved the unique and novel configurations and capabilities of the present invention. With these capabilities taken into consideration, the instant invention addresses many of the shortcomings of the prior art and offers significant benefits heretofore unavailable.

SUMMARY OF INVENTION

In its most general configuration, the present invention advances the state of the art with a variety of new capabilities and overcomes many of the shortcomings of prior methods in new and novel ways. In its most general sense, the present invention overcomes the shortcomings and limitations of the prior art in any of a number of generally effective configurations.

The present invention includes an ultrasonic testing (UT) method of identifying a stuck joint between a first workpiece and a second workpiece. The present method applies to all welds regardless of material, configuration, or the number of workpieces, as well as adhesive bonds regardless of material, configuration, or the number of workpieces. Thus, while the present disclosure generally refers to a stuck weld, one skilled in the art will appreciate that the present invention detects stuck portions of joints, which are often referred to as kissing bonds or weak bonds in the field of adhesives.

The present method utilizes an ultrasonic testing (UT) probe to transmit ultrasonic (US) beams into the joint area and capture the associated US reflections. The present invention utilizes the transmission of two separate US beams; namely, a primary US beam and a secondary US beam fired in very close proximity to one another, generally within a few milliseconds. The ultrasonic testing (UT) probe then captures a plurality of US reflections of the primary US beam and the secondary US beam.

A stuck joint occurs when the workpieces are held together by localized fusion at the welding interface, but no weld button is formed. The cause of stuck joints is generally when there is insufficient heat at the welding interface to bring about nugget growth. Instead, fusion occurs only between point contacts between the sheets. With coated materials, coatings can melt and refreeze, effectively soldering the parts together. The resulting bonds are strong enough to hold the workpieces together under light loads, but reasonable force will pull them apart. In the past, stuck joints have been particularly hard to identify using nondestructive evaluation (NDE) techniques. Adhesively bonded workpieces also have stuck joints, often referred to as kissing bonds, that may also be identified by the method of the present invention.

In a stuck joint, the US transmitted beams do pass through the interface between the workpieces. The present invention is a method for quickly and easily identifying a stuck weld by looking for subtle variations in the high gain A-scan presentation of the reflected beam. In fact, the invention incorporates a novel technique of using a low gain US beam that is transmitted with the high gain US beam to identify the particular location on the high gain A-scan presentation in which to look for signs of a stuck joint. It is these subtle variations within a particular region that allow the present invention to correctly identify stuck joints versus good welds.

The present invention utilizes the secondary US beam to assist in identifying the subtle variations that distinguish a stuck joint. In fact, the secondary US beam is used to precisely locate the position on the high gain A-scan presentation that should be analyzed for the subtle variations. Thus, in addition to creating a high gain A-scan presentation associated with the primary US beam, the present invention also creates a low gain A-scan presentation associated with the secondary US beam.

This method is applicable to metals and nonmetals alike. Further, it is not limited to fusion welding, but may also be used to examine solid state welds, brazed and soldered joints, and adhesively joined workpieces. Thus, while this method has particular application in the automated analysis of spot welds, it may also be used to evaluate continuous bonds.

Numerous variations, modifications, alternatives, and alterations of the various preferred embodiments, processes, and methods may be used alone or in combination with one another as will become more readily apparent to those with skill in the art with reference to the following detailed description of the preferred embodiments and the accompanying figures and drawings.

BRIEF DESCRIPTION OF THE DRAWINGS

Without limiting the scope of the present invention as claimed below and referring now to the drawings and figures:

DETAILED DESCRIPTION OF THE INVENTION

The UT method of identifying a stuck joint of the present invention enables a significant advance in the state of the art. The preferred embodiments of the method and system accomplish this by new and novel methods that are configured in unique and novel ways and which demonstrate previously unavailable but preferred and desirable capabilities. The description set forth below in connection with the drawings is intended merely as a description of the presently preferred embodiments of the invention, and is not intended to represent the only form in which the present invention may be constructed or utilized. The description sets forth the designs, functions, means, and methods of implementing the invention in connection with the illustrated embodiments. It is to be understood, however, that the same or equivalent functions and features may be accomplished by different embodiments that are also intended to be encompassed within the spirit and scope of the invention.

Figure 1:
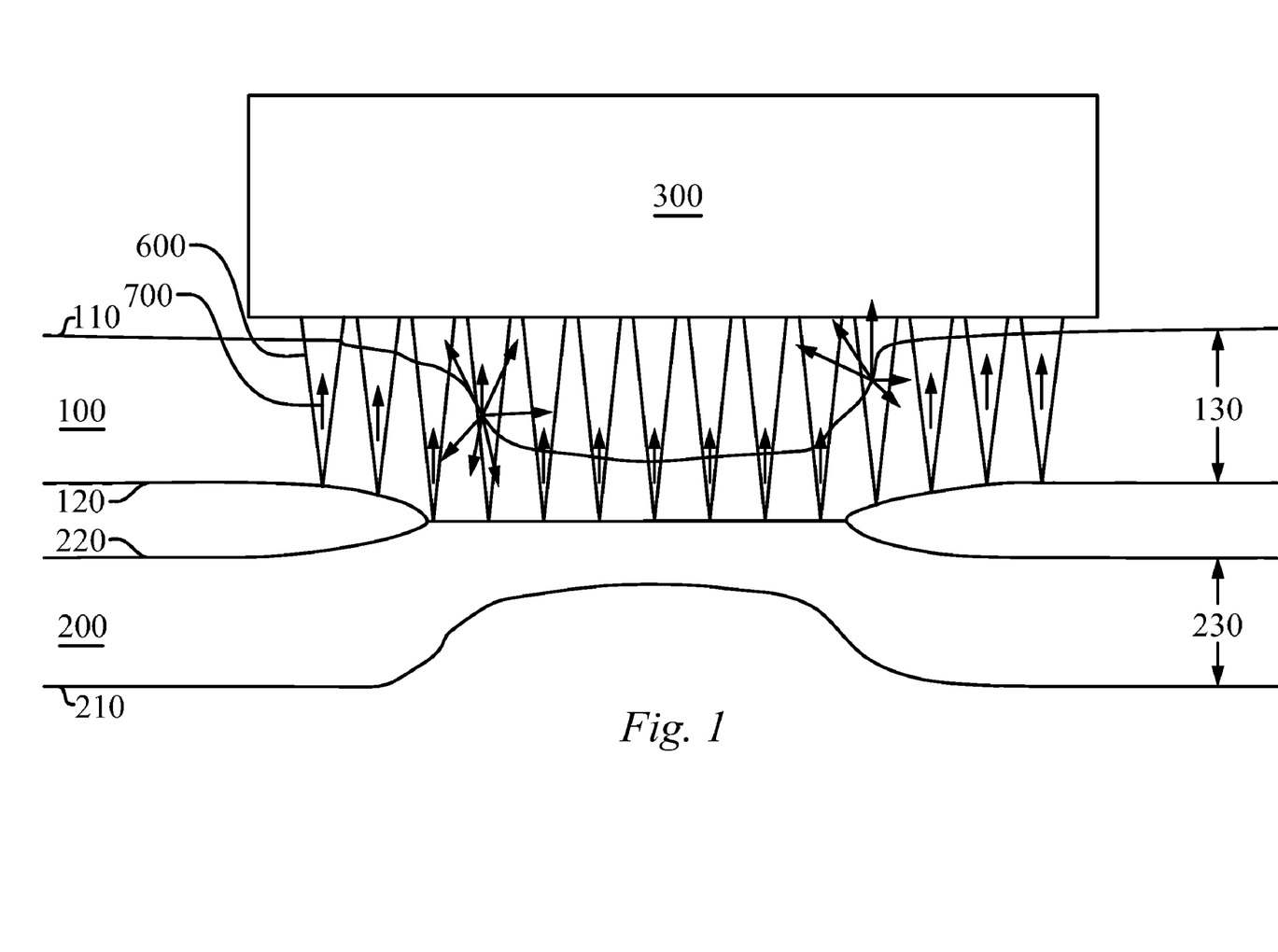
FIG. 1 shows a partial cross-sectional view and schematic of several elements of one embodiment of the method of the present invention applied to a joint having no fusion, not to scale.

Prior to discussing the method of the present invention, an introduction of the nomenclature used throughout this document is in order. Generally, the present invention is a UT method of identifying a stuck joint between a first workpiece (100) and a second workpiece (200), as seen in FIG. 1. While the figures and discussion herein refer to the joining of two sheet-like workpieces, one skilled in the art that the present method applies to all welds regardless of material, configuration, or the number of workpieces, as well as adhesive bonds regardless of material, configuration, or the number of workpieces. Thus, while the present disclosure generally refers to a stuck weld, one skilled in the art will appreciate that the present invention detects stuck portions of joints, which are often referred to as kissing bonds or weak bonds in the field of adhesives, In the illustrated embodiment of FIG. 1 the first workpiece (100) has a first workpiece exterior surface (110), a first workpiece interface surface (120), and a first workpiece thickness (130). Likewise, the second workpiece (200) has a second workpiece exterior surface (210), a second workpiece interface surface (220), and a second workpiece thickness (230). The first workpiece interface surface (120) and the second workpiece interface surface (220) are brought in contact with each other during the joining of the workpieces and the area of contact is generally referred to as the interface. Since the present invention is directed to a NDE method of analyzing the quality of the joint between the workpieces, it can be assumed that they are at least stuck to one another to some degree as the result of an attempted welding, brazing, soldering, or adhesive bonding operation.

Figure 2:
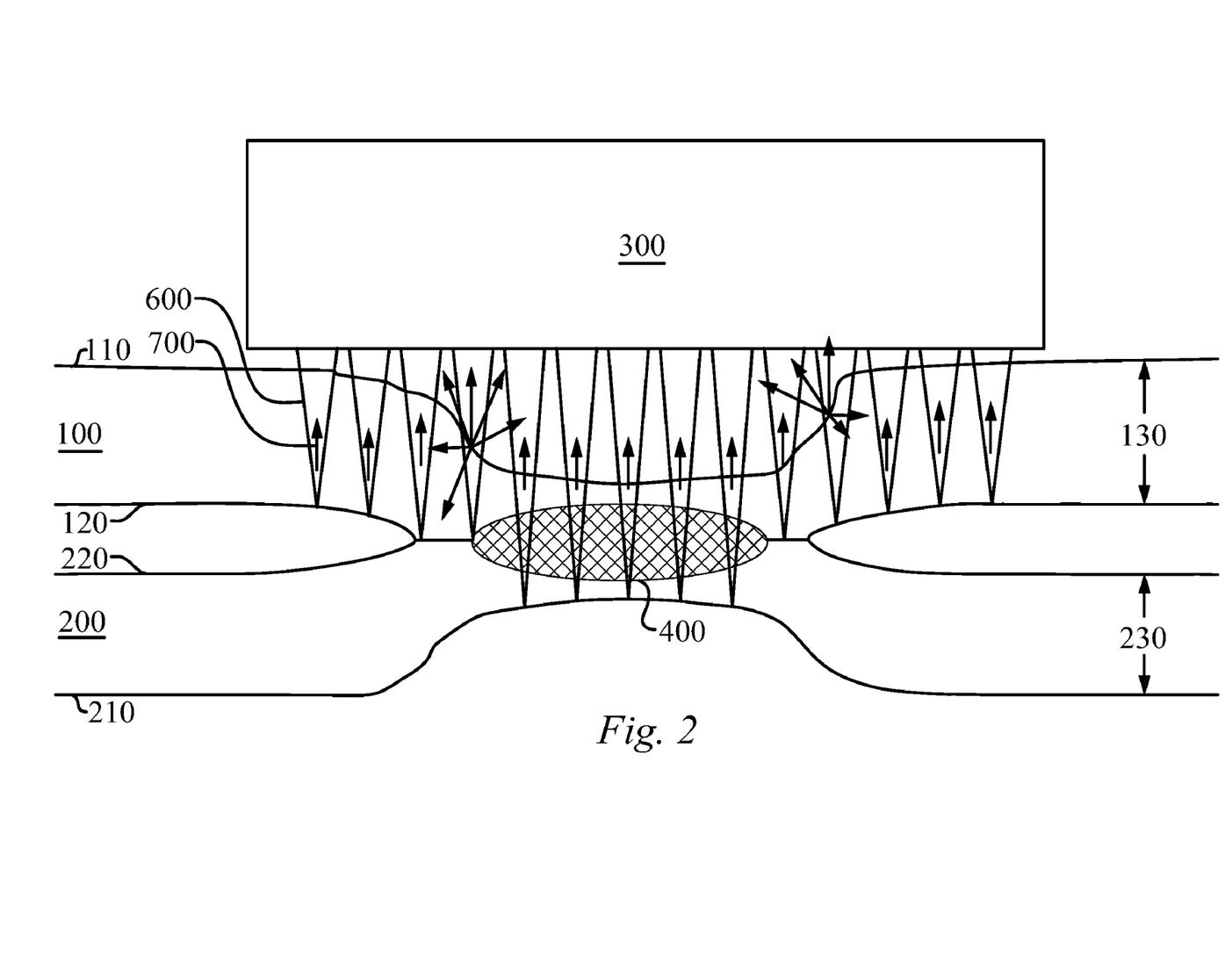
FIG. 2 shows a partial cross-sectional view and schematic of several elements of one embodiment of the method of the present invention applied to a joint having a good weld, not to scale.
Figure 3:
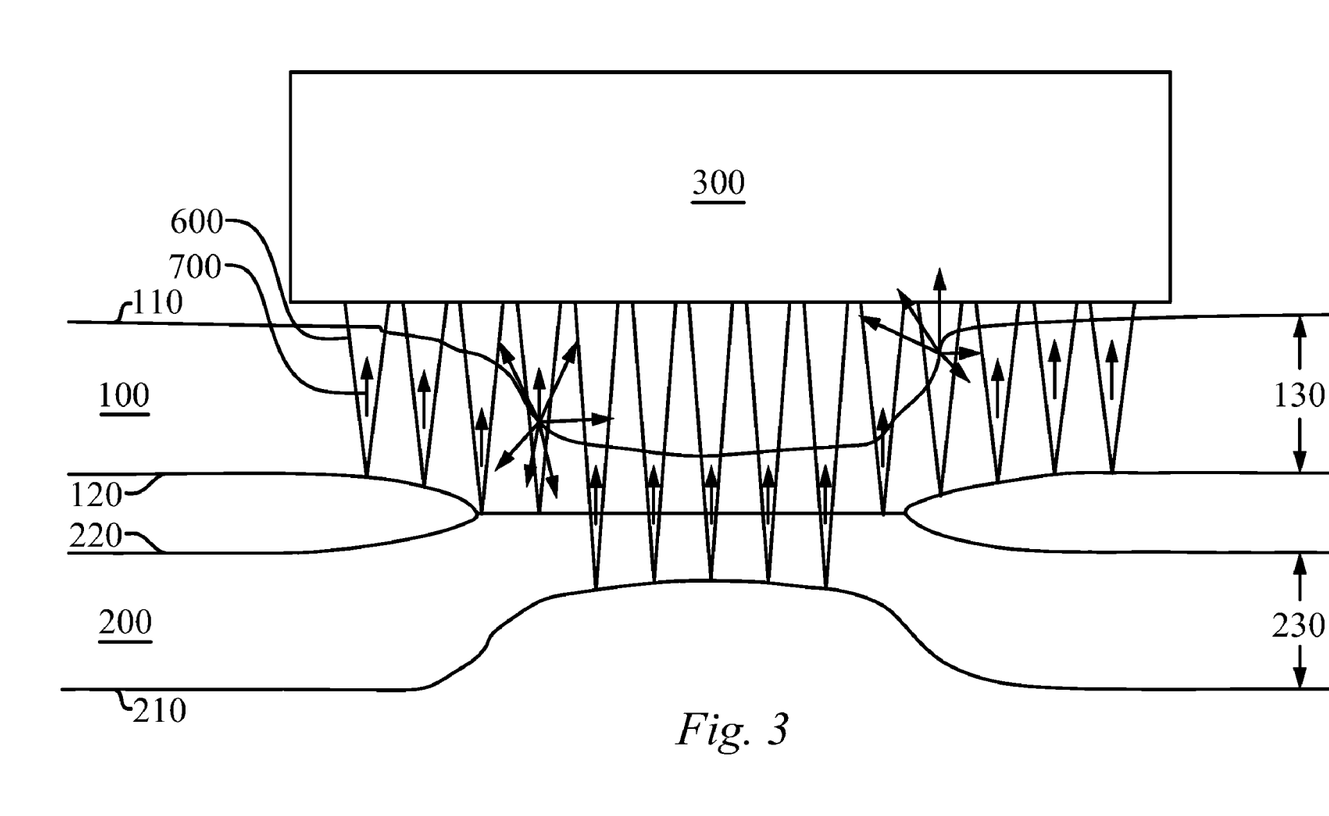
FIG. 3 shows a partial cross-sectional view and schematic of several elements of one embodiment of the method of the present invention applied to a joint having a stuck weld, not to scale.

The present method utilizes an ultrasonic testing (UT) probe (300) to transmit ultrasonic (US) beams into the joint area and capture the associated US reflections. The schematic figures of FIGS. 1-3 illustrate the transmitted beams (600) and the reflected beams (700). At this point it is important to understand that the present invention utilizes the transmission of two separate US beams; namely, a primary US beam and a secondary US beam fired in very close proximity to one another, generally within a few milliseconds. The ultrasonic testing (UT) probe (300) then captures a plurality of US reflections of the primary US beam and the secondary US beam.

The extent that the transmitted beams (600) penetrate an assembly in which the resistance spot welding process did not achieve fusion of the workpieces is schematically illustrated in FIG. 1. In this example the transmitted beams (600) extend from the first workpiece exterior surface (110) to the first workpiece interface surface (120) and do not cross the interface between the workpieces. This pattern of transmission and reflection produces a very distinct representation.

At this point, the collection and analysis of ultrasonic data should be disclosed before continuing with the description of the present invention. As one skilled in the art knows, ultrasonic data can be collected and displayed in a number of different formats. The three most common formats are known in the NDE world as A-scan, B-scan and C-scan presentations. Each presentation mode provides a different way of looking at and evaluating the region of material being inspected. The present invention utilizes the A-scan presentation.

The A-scan presentation displays the amount of received ultrasonic energy as a function of time. The relative amount of received energy is plotted along the vertical axis and the elapsed time (which may be related to the sound energy travel time within the material) is displayed along the horizontal axis. Most instruments with an A-scan display allow the signal to be displayed in its natural radio frequency form (RF), as a fully rectified RF signal, or as either the positive or negative half of the RF signal. In the A-scan presentation, relative discontinuity size can be estimated by comparing the signal amplitude obtained from an unknown reflector to that from a known reflector. Reflector depth can be determined by the position of the signal on the horizontal sweep.

Figure 4:
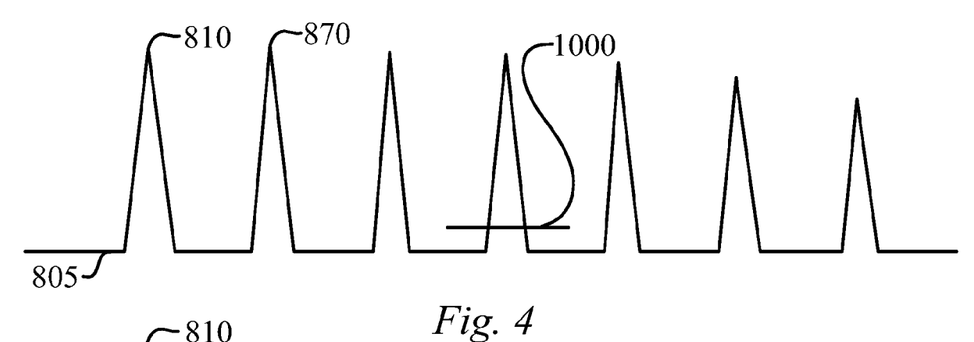
FIG. 4 shows a schematic representation of a high gain A-scan presentation of a joint having no fusion, not to scale.

Now, referring back to the assembly of FIG. 1 in which no fusion was achieved. A very simplified schematic of a high gain A-scan presentation (805) of this no fusion joint is seen in FIG. 4. The high gain A-scan presentation (805) firstly shows a high gain initial pulse representation (810) followed by a high gain single sheet back reflection representation (870), characteristic of the reflections from the first workpiece interface surface (120).

Figure 5:
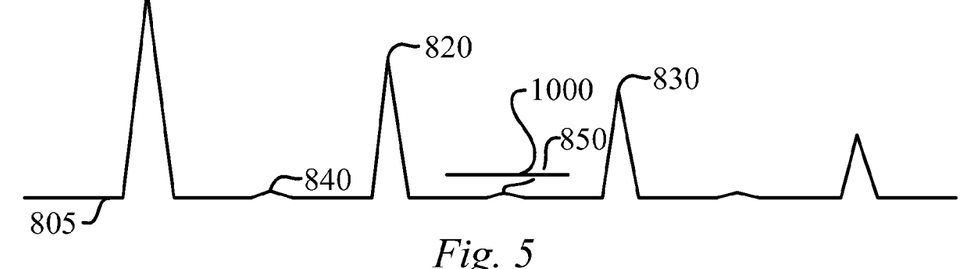
FIG. 5 shows a schematic representation of a high gain A-scan presentation of a joint having a good weld, not to scale.

Next, a good weld is shown in FIG. 2, with the associated high gain A-scan presentation (805) seen in FIG. 5. In this situation, a good weld nugget (400) allows the transmitted beams (600) to travel through the interface and reflect from the second workpiece exterior surface (210). The high gain A-scan presentation (805) of FIG. 5 illustrates a first peak at the high gain initial pulse representation peak (810), in other words the initial transmitted beam (600), followed by a minor spike at a first high gain interface reflection representation (840), then a first high gain full back reflection representation (820) representing the reflection from the second workpiece exterior surface (210), followed by a second high gain interface reflection representation (850), and then a second high gain full back reflection representation (830), and so on.

Figure 6:
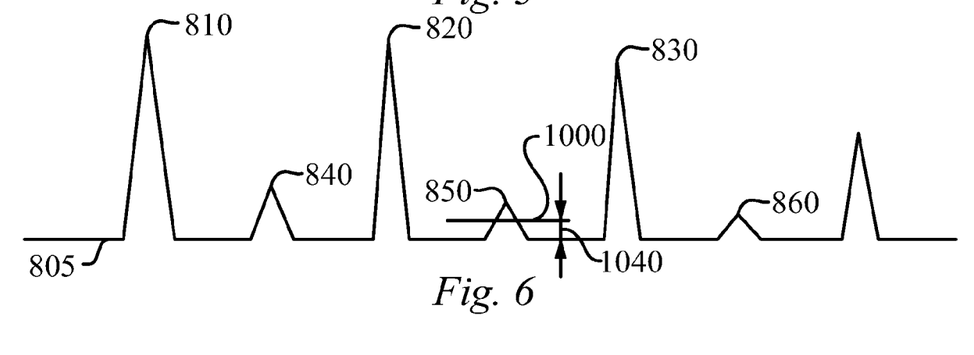
FIG. 6 shows a schematic representation of a high gain A-scan presentation of a joint having a stuck weld, not to scale.
Figure 7:
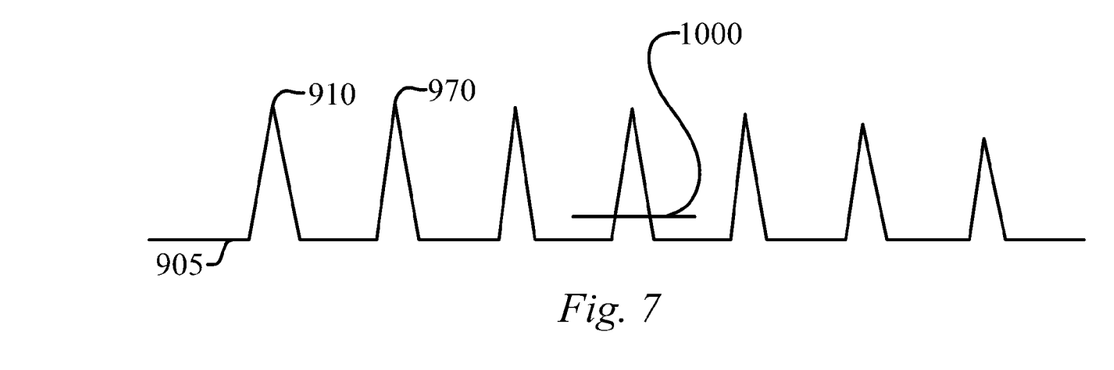
FIG. 7 shows a schematic representation of a low gain A-scan presentation of a joint having no fusion, not to scale.
Figure 8:
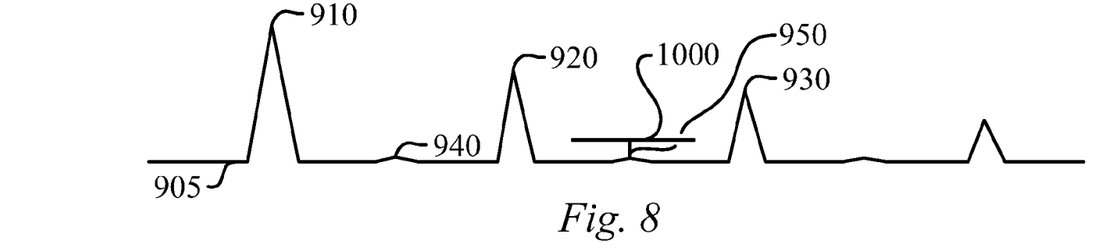
FIG. 8 shows a schematic representation of a low gain A-scan presentation of a joint having a good weld, not to scale.
Figure 9:
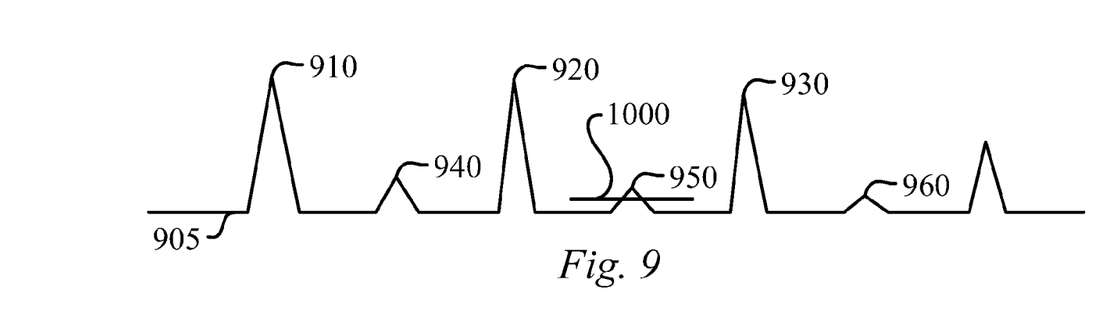
FIG. 9 shows a schematic representation of a low gain A-scan presentation of a joint having a stuck weld, not to scale.
Figure 10:
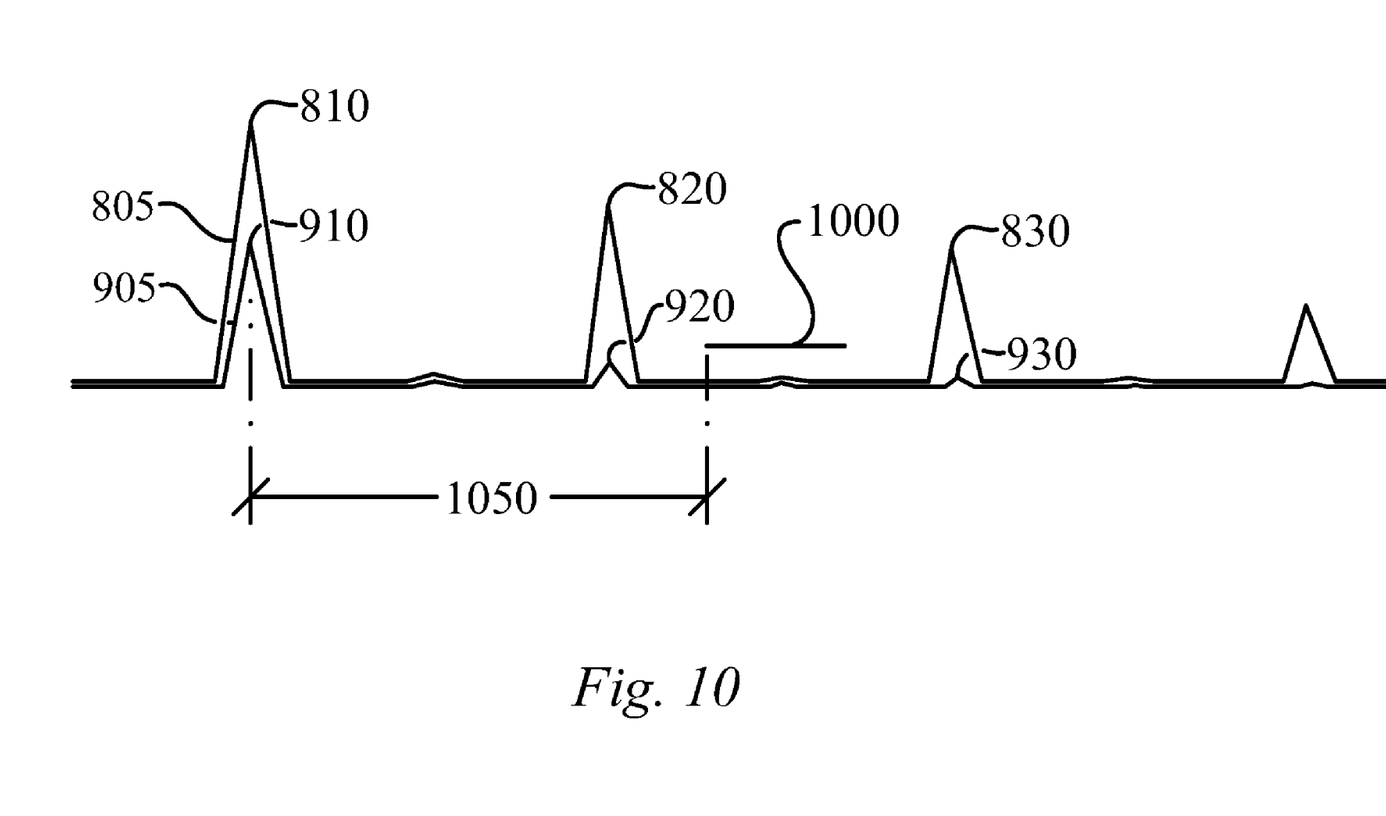
FIG. 10 shows a schematic representation of a low gain A-scan presentation and a high gain A-scan presentation of a joint having a good weld, not to scale.

Finally, a stuck weld, or stuck joint, is illustrated in FIG. 3, with the associated high gain A-scan presentation (805) seen in FIG. 6. A stuck joint occurs when the workpieces are held together by localized fusion at the welding interface, but no weld button is formed. The cause of stuck joints is generally when there is insufficient heat at the welding interface to bring about nugget growth. Instead, fusion occurs only between point contacts between the sheets. With coated materials, coatings can melt and refreeze, effectively soldering the parts together. The resulting bonds are strong enough to hold the workpieces together under light loads, but reasonable force will pull them apart. In the past, stuck joints have been particularly hard to identify using NDE techniques. Adhesively bonded workpieces also have stuck joints, often referred to as kissing bonds, that may also be identified by the method of the present invention.

In a stuck joint, such as that of FIG. 3, the US transmitted beams (600) do pass through the interface and reflect off the second workpiece exterior surface (210). The present invention is a method for quickly and easily identifying a stuck weld by looking for subtle variations in the high gain A-scan presentation (805) of the reflected beam (700). In fact, the invention incorporates a novel technique of using a low gain US beam that is transmitted with the high gain US beam to identify the particular location on the high gain A-scan presentation (805) in which to look for signs of a stuck joint.

Figure 11:
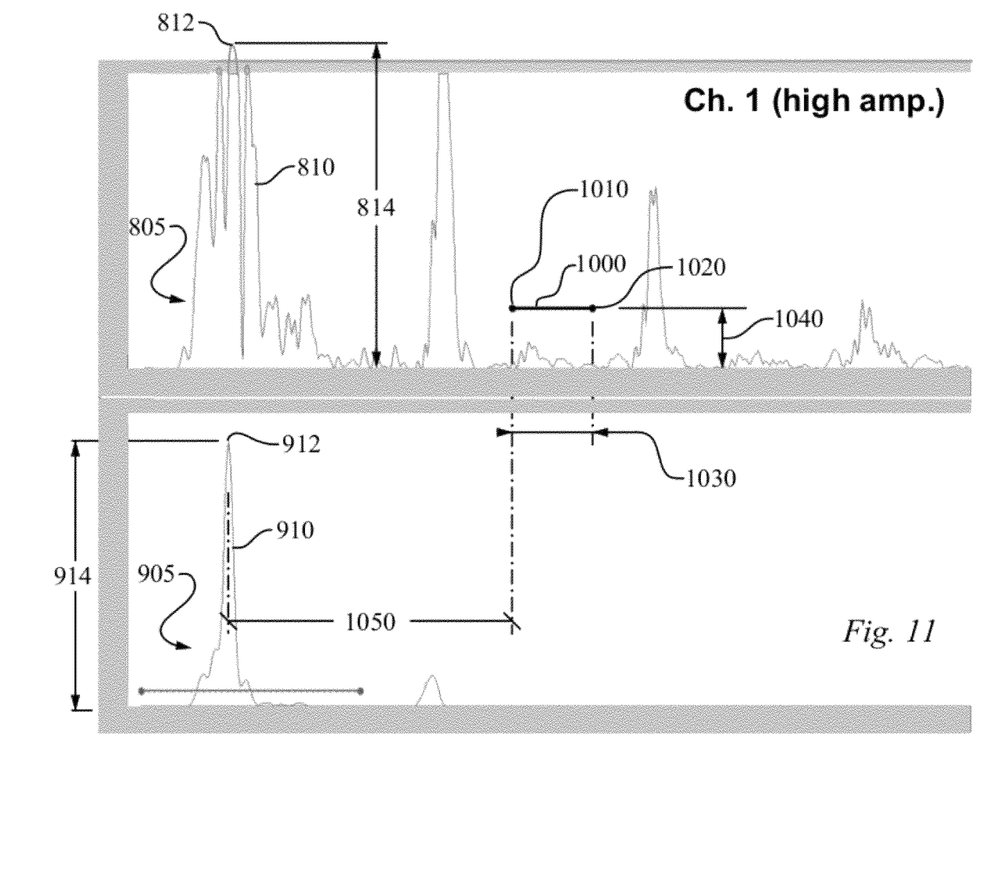
FIG. 11 shows a schematic representation of a low gain A-scan presentation and a high gain A-scan presentation of a joint having a good weld, not to scale.

Referring back to FIG. 6, the stuck joint high gain A-scan presentation (805) is very similar to the good weld high gain A-scan presentation (805) of FIG. 5. In fact, only minor variations in the amplitudes of the peaks differ between the presentations of FIG. 5 and FIG. 6. However, it is these subtle variations that allow the present invention to correctly identify stuck joints versus good welds. It is important to note that the high gain A-scan presentations (805) of FIGS. 4, 5, and 6 are extremely oversimplified. In practice, actual high gain A-scan presentations (805) are very choppy, as seen in FIG. 11, and therefore very difficult to use in identifying slight variations.

The present invention utilizes the secondary US beam to assist in identifying the subtle variations that distinguish a stuck joint. In fact, the secondary US beam is used to precisely locate the position on the high gain A-scan presentation (805) that should be analyzed for the subtle variations. Thus, in addition to creating a high gain A-scan presentation (805) associated with the primary US beam, the present invention also creates a low gain A-scan presentation (905) associated with the secondary US beam. The low gain A-scan presentation (905) is illustrated in FIGS. 7-11.

As with FIGS. 4-6 with respect to the high gain A-scan presentation (805), the low gain A-scan presentation (905) illustrated in FIGS. 7-10 is also very schematic and simplified. An actual low gain A-scan presentation (905) is shown in FIG. 11. The low gain A-scan presentation (905) has a low gain initial pulse representation (910), a low gain initial pulse representation peak (912), and a low gain initial pulse representation amplitude (914), as seen in FIG. 11. The low gain A-scan presentation (905) is incredibly less choppy than the high gain A-scan presentation (805), and therefore the low gain initial pulse representation peak (912) is significantly easier to accurately locate than the high gain initial pulse representation peak (812).

The ability to accurately locate the low gain initial pulse representation peak (912) facilitates the proper identification of the area of the high gain A-scan presentation (805) that should be analyzed for the characteristics of a stuck weld; this area is referred to as an interface detection gate (1000). The interface detection gate (1000) is positioned on the high gain A-scan presentation (805) located a gate offset distance (1050) from the low gain initial pulse representation peak (912) to a gate opening point (1010). The interface detection gate (1000) has a gate period (1030) defined by the gate opening point (1010) and a gate closing point (1020), and a gate amplitude (1040).

Next, the high gain A-scan presentation (805) within the interface detection gate (1000) is analyzed and a stuck joint portion alert is created if a portion of the high gain A-scan presentation (805) exceeds the gate amplitude (1040) within the interface detection gate (1000). Thus, the portion of the joint being examined is flagged if a stuck joint is indicated. Thus, in summary, the transmission of a primary US beam and a secondary US beam facilitates the creation of a high gain A-scan presentation (805) and a low gain A-scan presentation (905). A low gain initial pulse representation (910) is then used to position an interface detection gate (1000) on the high gain A-scan presentation (805). The high gain A-scan presentation (805) is then analyzed within the gate opening point (1010) and the gate closing point (1020). If the high gain A-scan presentation (805) exceeds the gate amplitude (1040) within the gate period (1030) then a stuck portion of a joint has been identified. Thus, the high gain A-scan presentation (805) of FIG. 6 illustrates a stuck portion of a joint wherein the second high gain interface reflection representation (850) magnitude exceeds the gate amplitude (1040).

The gate offset distance (1050) from the low gain initial pulse representation peak (912) to a gate opening point (1010) may be selected for any number of situations, but the interface detection gate (1000) is always selected to analyze at least one of the multiple interface reflection representations (840, 850, 860). Which interface representation (840, 850, 860) that is analyzed often depends on the type of material, the material thickness, and the number of layers that have been joined.

In one embodiment the at least one high gain interface reflection representation that is analyzed is a first high gain interface reflection representation (840) between the high gain initial pulse representation (810) and a first high gain full back reflection representation (820). In an alternative embodiment, seen in FIG. 6, the at least one high gain interface reflection representation that is analyzed is a second high gain interface reflection representation (850) between a first high gain full back reflection representation (820) and a second high gain full back reflection representation (830). In yet a further alternative embodiment, the at least one high gain interface reflection representation that is analyzed is a third high gain interface reflection representation (860) beyond a second high gain full back reflection representation (830).

Further, the gate period (1030) is adjustable such that only the desired portion of the high gain A-scan presentation (805) is analyzed. The gate period (1030) depends on the type of material, the material thickness, and the number of layers that have been joined. In one particular embodiment the gate period (1030) is less than fifty percent of the gate offset distance (1050). In an even further embodiment the gate period (1030) is less than thirty-five percent of the gate offset distance (1050).

In addition to the location of the interface detection gate (1000), the gate amplitude (1040) plays a significant role in determining whether a weld is a good weld or a stuck weld. In one embodiment a gate amplitude (1040) that is greater than 15 percent of the high gain initial pulse representation amplitude (814) and less than 40 percent of the high gain initial pulse representation amplitude (814) has been particularly effective in identifying stuck welds. In an even further embodiment the gate amplitude (1040) is greater than 20 percent of the high gain initial pulse representation amplitude (814) and less than 30 percent of the high gain initial pulse representation amplitude (814).

Figure 12:
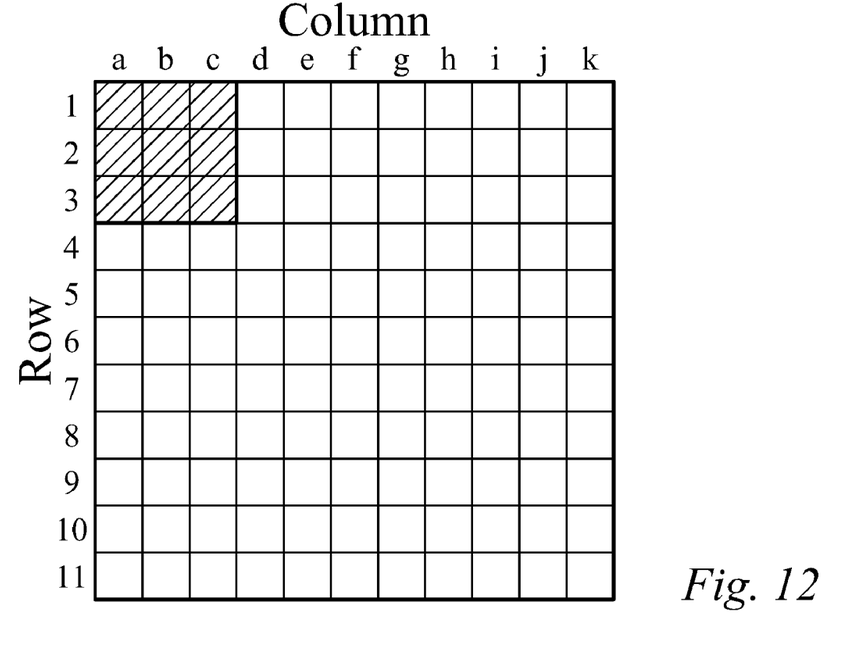
FIG. 12 is a schematic representation of a 121 element matrix phased array ultrasonic testing probe.

Further, the ultrasonic testing probe (300) may be virtually any ultrasonic testing probe. However, in one embodiment it is a high-frequency two-dimensional matrix phased-array probe, which offers additional capabilities to the present method. For instance, FIG. 12 schematically illustrates a 121 element matrix phased-array UT probe laid out in an eleven by eleven array; namely, eleven columns labeled a through k, and eleven rows labeled 1 through 11. Utilizing a high-frequency two-dimensional phased-array probe allows the collection and analysis of multiple high gain A-scan presentations (805) and multiple low gain A-scan presentations (905) in a fraction of a second.

In the past, commercially available UT systems for inspection of spot welds used high-frequency, single-crystal transducers or array transducers working in pulse-echo mode. Different transducers for different-sized welds are required using the conventional transducers in order to receive an integrated response from the weld area. In contrast to the conventional UT method, phased-array UT technology uses a probe (transducer) with many piezoelectric elements that are pulsed using programmed delay times.

In this embodiment, the high-frequency two-dimensional matrix phased-array probe uses an array of elements that are pulsed with different delays and generates an ultrasonic beam that can be focused, steered, and electronically scanned. This embodiment offers the ability to steer the beam in three-dimensional (3-D) space; to focus the beam in spherical, elliptical, or linear patterns; to focus the beam at different depths and skew angles using the same wedge; and the two-plane steering capability available for simultaneous variation of both the refracted and skew angles of the ultrasonic beam.

Figure 13:
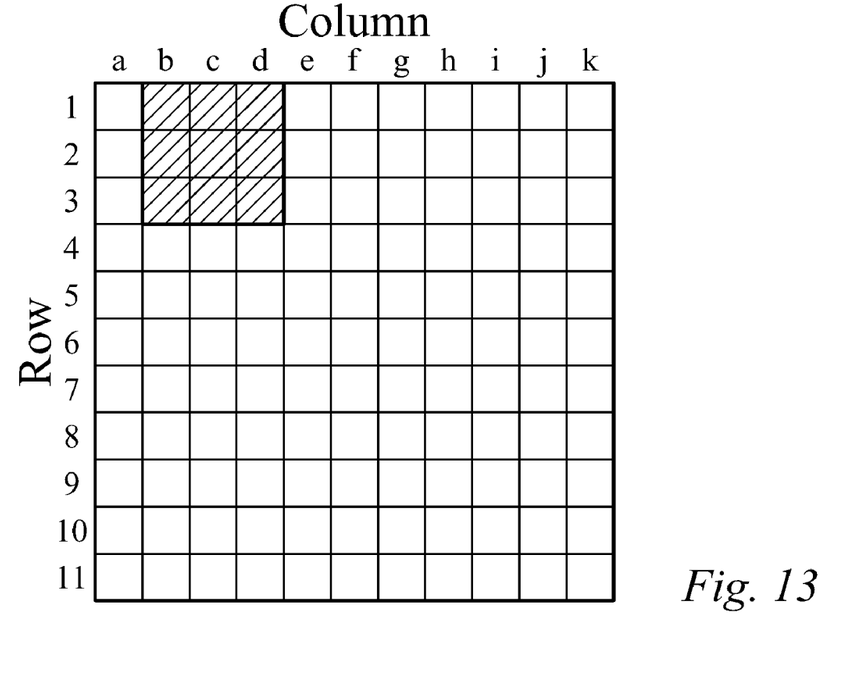
FIG. 13 is a schematic representation of a 121 element matrix phased array ultrasonic testing probe.

For instance, in one embodiment illustrated in FIG. 12, the 121 elements are electronically controlled to work in groups of nine, namely, a block of elements three wide and three high. In this embodiment the block of elements collects information from one portion of the joint which is used to create a high gain A-scan presentation (805) and a low gain A-scan presentation (905). The present method then determines if the portion of the joint associated with the information should be flagged as a stuck portion of the joint, and the block increments to the location of FIG. 13 to gather and analyze the same data for this block of elements.

One skilled in the art will recognize that if this process is continued with the 3 by 3 block of elements incrementing one element at a time, then the method would gather 81 high gain A-scan presentations (805) and 81 low gain A-scan presentations (905) as the block traverses across all 121 elements. Again, all of this data acquisition and analysis is performed in a fraction of a second. Thus, in this embodiment, each 3 by 3 block of elements is analyzing a portion of a joint and determining whether that portion of the joint should be flagged as a stuck portion of the joint. Then, the present method analyzes the information gathered for each portion of the joint to determine if the entire joint should be identified as a stuck joint. For example, if a predetermined percentage of the portions analyzed are flagged as stuck portions then the entire joint is flagged as a stuck joint. The predetermined percentage is experimentally determined and often varies depending on the type of material, the material thickness, and the number of layers that have been joined. Generally at least 10% of the portions analyzed would have to indicate the portion is a stuck portion for the entire joint to be identified as a stuck joint.

The 121 element matrix phased-array UT probe is just one example. One skilled in the art will appreciate that the present invention may utilize a single element probe, or at the opposite extreme it may utilize a probe containing thousands of elements. Further, the prior example illustrated the elements being grouped together in three element by three element groups. This grouping allows for electronically focusing and steering of the ultrasonic beam, however virtually any grouping of elements, or no grouping of elements at all, would also facilitate practicing the method of the present invention.

During discovery of the present invention resistance spot welds were studied. It was determined that in order to effectively image a 5 to 8 mm diameter spot weld from a single probe location, it was necessary to fully utilize maximum piezocomposite elements and have a probe footprint of approximately 175 square millimeters. In order to do this, the number of elements making up the aperture for each data point needed to be minimized. However, in order to achieve good electronic focusing in the desired focal depth range, a greater number of elements were needed. Beam models were generated to determine the minimum number of elements needed in the aperture to obtain sufficient electronic focusing. Generally a grouping of three elements by three elements or four elements by four elements is preferred.

As previously touched upon, this method is applicable to metals and nonmetals alike. Further, it is not limited to fusion welding, but may also be used to examine solid state welds, brazed and soldered joints, and adhesively joined workpieces. Thus, while this method has particular application in the automated analysis of spot welds, it may also be used to evaluate continuous bonds.

Numerous alterations, modifications, and variations of the preferred embodiments disclosed herein will be apparent to those skilled in the art and they are all anticipated and contemplated to be within the spirit and scope of the instant invention. For instance, while the disclosure herein always refers to two workpieces, one with skill in the art will appreciate that this invention may be utilized in the NDE of assemblies having more than two workpieces and the same principles apply. Further, although specific embodiments have been described in detail, those with skill in the art will understand that the preceding embodiments and variations can be modified to incorporate various types of substitute and or additional or alternative materials, relative arrangement of elements, and dimensional configurations. Accordingly, even though only few variations of the present invention are described herein, it is to be understood that the practice of such additional modifications and variations and the equivalents thereof, are within the spirit and scope of the invention as defined in the following claims. The corresponding structures, materials, acts, and equivalents of all means or step plus function elements in the claims below are intended to include any structure, material, or acts for performing the functions in combination with other claimed elements as specifically claimed.

We claim:

1. A UT method of identifying a stuck portion of a joint between a first workpiece and a second workpiece, comprising:
    transmitting a primary US beam and a secondary US beam from an ultrasonic testing probe into an assembly including the first workpiece and the second workpiece wherein the primary US beam is high gain and wherein the secondary US beam is low gain; and wherein the primary and secondary US beams are fired in within milliseconds of one another;
    capturing a plurality of US reflections of the primary US beam and the secondary US beam;
    creating a high gain A-scan presentation associated with the primary US beam and creating a low gain A-scan presentation associated with the secondary US beam;
    identifying a low gain initial pulse representation on the low gain A-scan presentation and identifying a low gain initial pulse representation peak;
    allocating an interface detection gate on the high gain A-scan presentation located a gate offset distance from the low gain initial pulse representation peak to a gate opening point, wherein the interface detection gate has a gate period defined by the gate opening point and a gate closing point, and wherein the interface detection gate has a gate amplitude; and
    analyzing the high gain A-scan presentation within the interface detection gate and creating a stuck joint portion alert if a portion of the high gain A-scan presentation exceeds the gate amplitude within the interface detection gate.

2. The method of claim 1, wherein the gate offset distance positions the interface detection gate in the proximity of at least one high gain interface reflection representation.

3. The method of claim 2, wherein the at least one high gain interface reflection representation is a first high gain interface reflection representation between the high gain initial pulse representation and a first high gain full back reflection representation.

4. The method of claim 2, wherein the at least one high gain interface reflection representation is a second high gain interface reflection representation between a first high gain full back reflection representation and a second high gain full back reflection representation.

5. The method of claim 2, wherein the at least one high gain interface reflection representation is a third high gain interface reflection representation beyond a second high gain full back reflection representation.

6. The method of claim 1, wherein the gate period is less than fifty percent of the gate offset distance.

7. The method of claim 1, wherein the gate period is less than thirty-five percent of the gate offset distance.

8. The method of claim 1, wherein the high gain A-scan presentation includes a high gain initial pulse representation that has a high gain initial pulse representation peak and a high gain initial pulse representation amplitude, wherein the gate amplitude is greater than 15 percent of the high gain initial pulse representation amplitude and less than 40 percent of the high gain initial pulse representation amplitude.

9. The method of claim 1, wherein the high gain A-scan presentation includes a high gain initial pulse representation that has a high gain initial pulse representation peak and a high gain initial pulse representation amplitude, wherein the gate amplitude is greater than 20 percent of the high gain initial pulse representation amplitude and less than 30 percent of the high gain initial pulse representation amplitude.

10. The method of claim 1, wherein the ultrasonic testing probe is a high-frequency two-dimensional matrix phased-array probe.

11. The method of claim 10, wherein the high-frequency two-dimensional matrix phased-array probe includes at least 100 piezocomposite elements.

12. The method of claim 11, wherein at least 9 piezocomposite elements of the at least 100 piezocomposite elements are electronically grouped together to create an aperture to electronically focus and steer the primary US beam and the secondary US beam.

13. The method of claim 11, wherein at least 16 piezocomposite elements of the at least 100 piezocomposite elements are electronically grouped together to create an aperture to electronically focus and steer the primary US beam and the secondary US beam.

14. The method of claim 1, wherein the joint between the first workpiece and the second workpiece is divided into at least 81 joint portions that are individually analyzed and each joint portion may create a distinct stuck joint portion alert.

15. The method of claim 14, wherein a stuck joint alert is created if the number of distinct stuck joint portion alerts exceeds 10 percent of the number of joint portions.

16. A UT method of identifying a stuck portion of a joint between a first workpiece and a second workpiece, comprising:
    transmitting a primary US beam and a secondary US beam from an ultrasonic testing probe into an assembly including the first workpiece and the second workpiece, wherein the ultrasonic testing probe is a high-frequency two-dimensional matrix phased-array probe; wherein the primary US beam is high gain and wherein the secondary US beam is low gain; and wherein the primary and secondary US beams are fired in within milliseconds of one another;
    capturing a plurality of US reflections of the primary US beam and the secondary US beam;
    creating a high gain A-scan presentation associated with the primary US beam and creating a low gain A-scan presentation associated with the secondary US beam, wherein the high gain A-scan presentation includes a high gain initial pulse representation that has a high gain initial pulse representation peak and a high gain initial pulse representation amplitude;
    identifying a low gain initial pulse representation on the low gain A-scan presentation and identifying a low gain initial pulse representation peak;
    allocating an interface detection gate on the high gain A-scan presentation located a gate offset distance from the low gain initial pulse representation peak to a gate opening point, wherein the interface detection gate has a gate period defined by the gate opening point and a gate closing point, and wherein the interface detection gate has a gate amplitude that is greater than 15 percent of the high gain initial pulse representation amplitude and less than 40 percent of the high gain initial pulse representation amplitude, and wherein the gate offset distance positions the interface detection gate in the proximity of at least one high gain interface reflection representation, and wherein the gate period is less than fifty percent of the gate offset distance; and analyzing the high gain A-scan presentation within the interface detection gate and creating a stuck joint portion alert if a portion of the high gain A-scan presentation exceeds the gate amplitude within the interface detection gate.

17. The method of claim 16, wherein the at least one high gain interface reflection representation is a first high gain interface reflection representation between the high gain initial pulse representation and a first high gain full back reflection representation.

18. The method of claim 16, wherein the high-frequency two-dimensional matrix phased-array probe includes at least 100 piezocomposite elements.

19. The method of claim 18, wherein at least 9 piezocomposite elements of the at least 100 piezocomposite elements are electronically grouped together to create an aperture to electronically focus and steer the primary US beam and the secondary US beam.

20. A UT method of identifying a stuck portion of a joint between a first workpiece and a second workpiece, comprising:

transmitting a primary US beam and a secondary US beam from an ultrasonic testing probe into an assembly including the first workpiece and the second workpiece, wherein the ultrasonic testing probe is a high-frequency two-dimensional matrix phased-array probe including at least 100 piezocomposite elements and at least 9 piezocomposite elements of the at least 100 piezocomposite elements are electronically grouped together to create an aperture to electronically focus and steer the primary US beam and the secondary US beam, and wherein the joint between the first workpiece and the second workpiece is divided into at least 81 joint portions; wherein the primary US beam is high gain and wherein the secondary US beam is low gain; and wherein the primary and secondary US beams are fired in within milliseconds of one another;

capturing a plurality of US reflections of the primary US beam and the secondary US beam for each joint portion;

creating a high gain A-scan presentation associated with the primary US beam and creating a low gain A-scan presentation associated with the secondary US beam for each joint portion, wherein the high gain A-scan presentation includes a high gain initial pulse representation that has a high gain initial pulse representation peak and a high gain initial pulse representation amplitude;

identifying a low gain initial pulse representation on the low gain A-scan presentation and identifying a low gain initial pulse representation peak for each joint portion;

allocating an interface detection gate on the high gain A-scan presentation of each joint portion located a gate offset distance from the low gain initial pulse representation peak to a gate opening point, wherein each interface detection gate has a gate period defined by the gate opening point and a gate closing point, and wherein each interface detection gate has a gate amplitude that is greater than 15 percent of the high gain initial pulse representation amplitude and less than 40 percent of the high gain initial pulse representation amplitude, and wherein each gate offset distance positions each interface detection gate in the proximity of at least one high gain interface reflection representation, and wherein each gate period is less than fifty percent of each gate offset distance; and analyzing each high gain A-scan presentation within the associated interface detection gate and creating a stuck joint portion alert if a portion of the high gain A-scan presentation exceeds the gate amplitude within the interface detection gate, and creating a stuck joint alert if the number of distinct stuck joint portion alerts exceeds 10 percent of the number of joint portions.

* * * * *